United States Patent
Liu et al.

(10) Patent No.: US 7,204,128 B1
(45) Date of Patent: Apr. 17, 2007

(54) ENGINE WEAR AND OIL QUALITY SENSOR

(76) Inventors: James Z T Liu, 267 Lowell, Hudson, NH (US) 03051; Aziz Rahman, 36 Old Wolomolopoag, Sharon, MA (US) 02067; Michael L. Rhodes, 7526 5th Ave., Richfield, MN (US) 55423

( * ) Notice: Subject to any disclaimer, the term of this patent is extended or adjusted under 35 U.S.C. 154(b) by 0 days.

(21) Appl. No.: 11/244,945

(22) Filed: Oct. 5, 2005

(51) Int. Cl.
*G01N 11/00* (2006.01)
*G01N 33/487* (2006.01)

(52) U.S. Cl. ............... 73/53.01; 73/54.24; 73/649
(58) Field of Classification Search ........... 73/53.01, 73/649
See application file for complete search history.

(56) References Cited

U.S. PATENT DOCUMENTS

| | | | |
|---|---|---|---|
| 4,691,714 A * | 9/1987 | Wong et al. | 600/551 |
| 4,782,332 A | 11/1988 | Cipris et al. | 340/603 |
| 4,792,791 A | 12/1988 | Cipris et al. | 340/603 |
| 5,117,146 A * | 5/1992 | Martin et al. | 310/313 R |
| 5,235,235 A * | 8/1993 | Martin et al. | 310/313 D |
| 5,274,335 A | 12/1993 | Wang et al. | 324/689 |
| 5,301,643 A | 4/1994 | Garcyalny | 123/198 D |
| 5,336,396 A | 8/1994 | Shetley | 210/90 |
| 5,604,441 A * | 2/1997 | Freese et al. | 324/663 |
| 5,869,763 A | 2/1999 | Vig et al. | 73/580 |
| 5,878,708 A | 3/1999 | Ruman | 123/196 M |
| 6,044,332 A | 3/2000 | Korsah et al. | 702/76 |
| 6,076,406 A | 6/2000 | Blair et al. | 73/590 |
| 6,260,408 B1 * | 7/2001 | Vig et al. | 73/64.53 |
| 6,293,136 B1 * | 9/2001 | Kim | 73/19.03 |
| 6,508,100 B2 | 1/2003 | Berndorfer | 73/1.02 |
| 6,557,396 B2 | 5/2003 | Ismail et al. | 73/53.05 |
| 6,776,024 B2 | 8/2004 | Jakoby | 73/10 |
| 6,786,080 B2 | 9/2004 | Jakoby et al. | 73/54.01 |
| 6,799,458 B2 | 10/2004 | Ismail et al. | 73/304 C |
| 6,873,916 B2 * | 3/2005 | Kolosov et al. | 702/25 |
| 2004/0035398 A1 | 2/2004 | Klugl et al. | 123/456 |
| 2005/0030332 A1 * | 2/2005 | Masuda | 347/19 |
| 2005/0262944 A1 * | 12/2005 | Bennett et al. | 73/592 |
| 2006/0230834 A1 * | 10/2006 | Liu et al. | 73/649 |
| 2006/0243032 A1 * | 11/2006 | Liu et al. | 73/53.05 |

OTHER PUBLICATIONS

"An Acoustic Automotive Engine Oil Quality Sensor", J. M. Hammond, R. M. Lec, X. J. Zhang, D. G. Libby and L. A. Prager, Department of Electrical and Computer Engineering, University of Maine, 1997.*

(Continued)

*Primary Examiner*—Hezron Williams
*Assistant Examiner*—Samir M. Shah
(74) *Attorney, Agent, or Firm*—Kermit D. Lopez; Luis M. Ortiz

(57) ABSTRACT

A viscosity and corrosivity sensor apparatus includes a substrate upon which one or more electrodes are configured. The electrode(s) are exposed to a liquid, such as automotive oil. An oscillator can be connected to the electrode, wherein the oscillator assists in providing data indicative of the corrosivity and data indicative of the viscosity of the liquid in contact with the electrode(s). A viscosity and corrosivity sensor is therefore provided in the same package.

20 Claims, 2 Drawing Sheets

OTHER PUBLICATIONS

"SAW Devices as Wireless Passive Sensors", L. Reindl, G. Scholl, T. Ostertag, C. C. W. Ruppel, W. E. Bulst and F. Seifert, Siemens AG Corporate REsearch and Development, Munich, Germany, 1996.*

"Temperature-Insensitive Dual-Mode Resonant Sensors—A Review", John R. Vig, U.S. Government work, Jun. 2001.*

"An Automotive Engine Oil Viscosity Sensor", Bernhard Jakoby, Monika Scherer, Matthias Buskies and Hainz Eisenschmid, IEEE Sensors Journal, vol. 3. No. 5, Oct. 2003.*

"A Remote Acoustic Engine Oil Quality Sensor", R. M. Lec, X. J. Zhang and J. M. Hammond, University of Maine, 1997.*

"Sensing the Properties of Liquids with Doubly Rotated Resonators", Yoonkee Kim, John R. Vig and Arthur Ballato, US Army Communications-Electronics Command, IEEE International Frequency Control Symposium, 1998.*

"Multi-Frequency and Multi-Mode GHz Surface Acoustic Wave Sensor", W. Seidel and T. Hesjedal, Paul Drude Institute for Solid State Electronics, IEEE Ultrasonics Symposium, 2003.*

* cited by examiner

ENGINE WEAR AND OIL QUALITY SENSOR

TECHNICAL FIELD

Embodiments are generally related to sensing devices. Embodiments are also related to etch rate sensors. Embodiments are additionally related to corrosivity and viscosity sensors. Embodiments are also related to sensors for measuring engine wear and lube oil quality data. Embodiments are additionally related to acoustic wave sensors.

BACKGROUND

Acoustic wave sensors are utilized in a variety of sensing applications, such as, for example, temperature and/or pressure sensing devices and systems. Acoustic wave devices have been in commercial use for over sixty years. Although the telecommunications industry is the largest user of acoustic wave devices, they are also used for sensor applications, such as in chemical vapor detection. Acoustic wave sensors are so named because they use a mechanical, or acoustic, wave as the sensing mechanism. As the acoustic wave propagates through or on the surface of the material, any changes to the characteristics of the propagation path affect the velocity, phase and/or amplitude of the wave.

Changes in acoustic wave characteristics can be monitored by measuring the frequency or phase characteristics of the sensor and can then be correlated to the corresponding physical quantity or chemical quantity that is being measured. Virtually all acoustic wave devices and sensors utilize a piezoelectric crystal to generate the acoustic wave. Three mechanisms can contribute to acoustic wave sensor response, i.e., mass-loading, visco-elastic and acousto-electric effect. The mass-loading of chemicals alters the frequency, amplitude, and phase and Q value of such sensors. Most acoustic wave chemical detection sensors, for example, rely on the mass sensitivity of the sensor in conjunction with a chemically selective coating that absorbs the vapors of interest resulting in an increased mass loading of the SAW sensor. Examples of acoustic wave sensors include acoustic wave detection devices, which are utilized to detect the presence of substances, such as chemicals, or environmental conditions such as temperature and pressure.

An acoustical or acoustic wave (e.g., SAW/BAW) device acting as a sensor can provide a highly sensitive detection mechanism due to the high sensitivity to surface loading and the low noise, which results from their intrinsic high Q factor. Surface acoustic wave (SAW/SH-SAW) and amplitude plate mode (APM/SH-APM) devices are typically fabricated using photolithographic techniques with comb-like interdigital transducers (IDTs) placed on a piezoelectric material. Surface acoustic wave devices may have a delay line, a filter or a resonator configuration. Bulk acoustic wave devices are typically fabricated using a vacuum plater, such as those made by CHA, Transat or Saunder. The choice of the electrode materials and the thickness of the electrode are controlled by filament temperature and total heating time. The size and shape of electrodes are defined by proper use of mask. Based on the foregoing, it can be appreciated that acoustic wave devices, such as a surface acoustic wave resonator (SAW-R), surface acoustic wave filter (SAW-filter), surface acoustic wave delay line (SAW-DL), surface transverse wave (STW), bulk acoustic wave (BAW), can be utilized in various sensing measurement applications.

One promising application for micro-sensors involves oil filter and oil quality monitoring. Except under very unusual circumstances, oil does not "wear out", "break down" or otherwise deteriorate to such an extent that it needs to be replaced. What happens is that it becomes contaminated with water, acids, burnt and un-burnt fuel, carbon particles and sludge so that is can no longer provide the desired degree of protection for engine components. Most oil filters in modern vehicles do not remove all the contaminants. A filter can only remove solid particles above a certain size. It cannot remove water, acids, or fuel dilution, all of which pass through the full-flow filter just as readily as the oil.

Motor oils are fortified with inhibitors to provide them with a remarkable stability and resistance to oxidation and deterioration. Such oils also contain acid neutralizing additives to eliminate acidity or engine corrosion. There is a limit, however, to the amount of contamination that even the best oil can neutralize, and there comes a time when the only satisfactory procedure is to drain the oil and replenish the engine with a new charge. Thus, there arises the necessity for regular oil changes.

The question is now "how often should engine oil be changed?" Unfortunately, there is no simple answer to this question. From the foregoing discussion, it is apparent that oil is changed not because it has deteriorated, but because it has become contaminated with various harmful substances, and that the greater the rate at which such substances enter the oil, the sooner an oil change is necessary.

Factors that influence the necessity of oil changes include engine conditions and the method of engine operation. A vehicle that is used mainly for short distance stop-start running will require more frequent oil changes than one used for regular long distance traveling. A warm engine with leaky piston rings, for example, can contaminate the oil quicker than a new engine in good mechanical condition.

It should also be kept in mind that a high performance product (e.g., more additives) can handle more contaminates than other products, and hence longer oil change periods can be justified. As a final comment on this subject, it is worth mentioning that it is normal for oil to darken in service. This is not an indication that the oil has deteriorated. This merely demonstrates that the oil has picked up contaminates and maintains them in suspension, where they can do no harm, and where they can be removed from the engine when the oil is changed.

In general, motor oil should perform two primary functions. The oil must lubricate the engine and also serve as a collector of contamination. The contamination comes from the engine combustion chambers where the gasoline is burned to produce powder. There are two different types of fuel combustion in engines: efficient combustion or clean burning; and inefficient combustion or dirty burning.

When dirty combustion occurs in an engine, soot is not the only product formed. Sticky, gummy products, which oil chemists refer to as resins, and lead oxyhalides, may also form. Small quantities of acidic combustion products may also be present. Water is also a factor. For every gallon of gasoline burned, a little over one gallon of water may be formed. Thus, during the burning of gasoline in engines, a potential problem exists with respect to soot, resins, acids, and water formation. If combustion products function past the pistons and manage to penetrate the crankcase oil, then a problem of dirty, contaminated oil will exist. If the oil is allowed to become too dirty and contaminated, sludge deposits can form, thereby resulting in plugged piston rings, oil pump screens and oil filters. Engine wear and even engine damage can then result.

A truck, bus or passenger car driven at highway speed on a long trip can easily be lubricated and is the least demanding on an oil of good quality. The really tough lubricating job is the engine, which typically experiences only short runs with numerous stops and starts, especially in cold weather. The worst conditions for both the engine and the oil are the very conditions under which the great majority of passenger cars are used most of the time.

Knowledge of the condition of oil in the field would obviously be extremely beneficial information to truck fleet maintenance managers and maintenance personnel. A permanently installed oil quality sensor system can deliver the above information.

Currently, fleets that do perform analysis on their lubes utilize complete laboratory oil analysis. Primarily due to the cost of laboratory analysis, however, these tests are only performed on a routine basis, i.e. monthly or at each oil drain interval. Laboratory oil analysis serves two basic functions. The first function is to monitor the condition of the lube oil. Lube oil within a healthy engine degrades at a slow rate with normal use. Therefore, lab analysis can provide a forewarning and allow for scheduling of routine oil drains. Complete lab analysis is very effective in accomplishing this goal and first function.

It is at the second function, however, where lab analysis fails and does not provide sufficient failure warnings such as coolant leaks and stress related metal failures. Equipment is normally sampled on a monthly basis and while this is a sufficient interval to safely monitor the lube condition, many times this frequency is not sufficient in detecting engine problems. After all, analysis is used to detect the "Problem" before "Failure" and "Downtime" can then occur.

An example of this situation is as follows. A company samples its equipment on a monthly basis. On the first day of the month a sample of the used oil is taken and sent to the lab for analysis. On the second day, unknown to the maintenance personnel and the oil lab, a coolant leak develops within the engine. The next scheduled time for another complete laboratory analysis sample to be taken is twenty-nine days away.

Within the next several days, the coolant leak degrades the oil within the engine to the point that it causes wear to occur to bearings and other parts of the engine. Somewhere between the seventh and the tenth day the operator receives the results from the lab sample taken on the first day of the month. These results were taken before the problem occurred and shows no problems within the engine and that the oil is suitable for further use. Two days after receiving this report, the operator notices that the oil is becoming cloudy and that the engine is making a little steam. The routine monthly sampling of the used oil was not effective in achieving its goal.

The need is immense for a permanently installed sensor device that can determine the condition of the lube and equipment which can be used on a more frequent basis than complete laboratory analysis sampling. This need can be met by the use of the disclosure here.

One promising application for micro-sensors involves oil filter and oil quality monitoring. Diesel engines are particularly hard on oil because of oxidation from acidic combustion. As the oil wears, it oxidizes and undergoes a slow build-up of total acids number (TAN). A pH sensor is capable of direct measurement of TAN and an indirect measurement of total base number (TBN), providing an early warning of oil degradation due to oxidation and excess of water. The acids and water build-up is also related to the viscosity of the oil.

Low temperature start-ability, fuel economy, thinning or thickening effects at high and/or low temperatures, along with lubricity and oil film thickness in running automotive engines are all dependent upon viscosity. Frequency changes in viscosity have been utilized in conventional oil detection systems. The frequency changes caused by small changes in viscosity of highly viscous liquids, however, are very small. Because of the highly viscous loading, the signal from a sensor oscillator is very "noisy" and the accuracy of such measurement systems is very poor. Moreover, such oscillators may cease oscillation due to the loss of the inductive properties of the resonator.

TAN is a property typically associated with industrial oils. It is defined as the amount of acid and acid-like material in the oil. Oxidation and nitration resins make up the majority of this material. As the oil is used, acidic components build up in the lubricant causing the TAN number to increase. A high TAN number represents the potential for accelerated rust, corrosion and oxidation and is a signal that the oil should be replaced. Critical TAN numbers are dependant on oil type.

There is a need to provide a sensor apparatus which can be utilized to monitor, in a sensitive manner, the etching effects of etchants, such as acids contained in oils. There is also a need to provide a sensor system which can monitor corrosion or degradation of engines or other devices caused by exposure to such etchants. It is believed that acoustic wave sensors may well be suited for such monitoring as indicated by the embodiments described herein.

One of the problems with acoustic wave devices utilized in oil monitoring applications, for example, is that frequency changes caused by small changes in the viscosity of highly viscous fluids, are very small. Because of highly viscous loading, the signal from an oscillator associated with the acoustic wave sensor device is very noisy and the accuracy of such measurements is very poor. Moreover, the oscillators may cease oscillation due to the loss of the inductive properties of the resonator.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for a combined viscosity and corrosivity sensor apparatus and system.

It is another aspect of the present invention to provide for a single sensor that can be utilized for multiple parameters measurement.

It is another aspect of the present invention to provide for a single sensor that accomplishes viscosity and etch rate measurements.

The aforementioned aspects of the invention and other objectives and advantages can now be achieved as described herein. A viscosity and corrosivity sensor apparatus is disclosed, which includes a substrate upon which one or more electrodes are configured. The electrode(s) are exposed to a liquid, such as automotive oil. An oscillator can be connected to the electrode, wherein the oscillator assists in providing data indicative of the corrosivity and data indicative of the viscosity of the liquid in contact with the electrode(s).

A resistance measurement component is also connected to the electrode and the oscillator. The electrodes can be provided in the form of a top electrode and a bottom electrode configured upon the substrate. Data indicative of the corrosivity is based on a frequency generated by the oscillator in association with the substrate and the electrode(s). Such a frequency is utilized to provide data indicative of the etch rate associated with the electrode(s). Data indicative of the viscosity of the liquid is generally based on the amplitude or phase generated by the oscillator in association with the substrate and the electrode(s). Additionally, an antenna can be connected to the viscosity and corrosivity sensor apparatus, wherein the antenna wirelessly transmits and receives data associated with and/or indicative of the detection of the viscosity and the corrosivity of the liquid.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
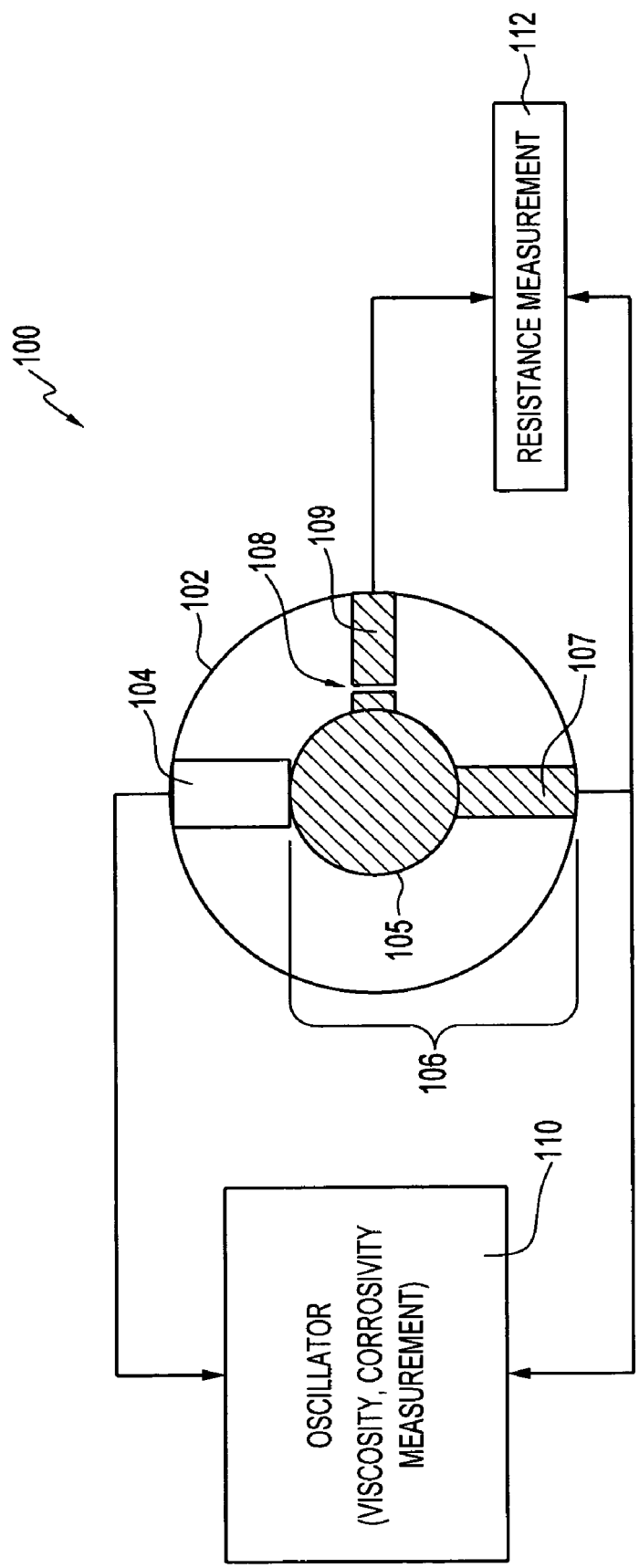
FIG. 1 illustrates a schematic diagram of a viscosity and corrosivity sensor apparatus that can be implemented in accordance with a preferred embodiment.

FIG. 1 illustrates a schematic diagram of a viscosity and corrosivity sensor apparatus 100 that can be implemented in accordance with a preferred embodiment. The viscosity and corrosivity sensor apparatus 100 generally includes a substrate 102 upon which one or more electrodes 104, 106 can be configured. Note that electrode 106 is generally composed of one or more electrode portions 105, 107, and 109. Electrode 104 functions as a bottom electrode and electrode 106 functions as a top electrode. A resistance measurement component 112 is connected to the electrode portion 109 of the top electrode 106, while an oscillator 110 is connected to the bottom electrode 104 and the resistance measurement component 112. The viscosity and corrosivity sensor apparatus 100 can be adapted for use in monitoring engine wear in an automotive system by analyzing, for example, oil exposed to electrodes 104, 106 as indicated in greater detail herein. Note that the electrodes 104, 106 can be formed on substrate 102 by various deposition techniques, for example by physical vapor deposition (PVD), chemical vapor deposition (CVD), and sputtering or electrode chemical deposition.

The resistance measurement component is generally utilized to obtain conductivity information. The oscillator 110 is utilized for viscosity and corrosivity measurement. Frequency is utilized to obtain etch rate data or corrosivity data. Amplitude or phase measurement is utilized to obtain viscosity data. The oscillator 110 thus assists in providing data indicative of the corrosivity and/or viscosity of a liquid in contact with electrodes 104 and/or 106. A gap 108 is generally located between electrode portions 105 and 109 of electrode 106. Gap 108 can be implemented as, for example, a 30 to 100 um gap for conductivity measurement purposes associated with the resistance measurement component 112. Note that oscillator 110 can be provided as a Surface Acoustic Wave (SAW) or Bulk Acoustic Wave (BAW) oscillator, depending upon design considerations.

Figure 2:
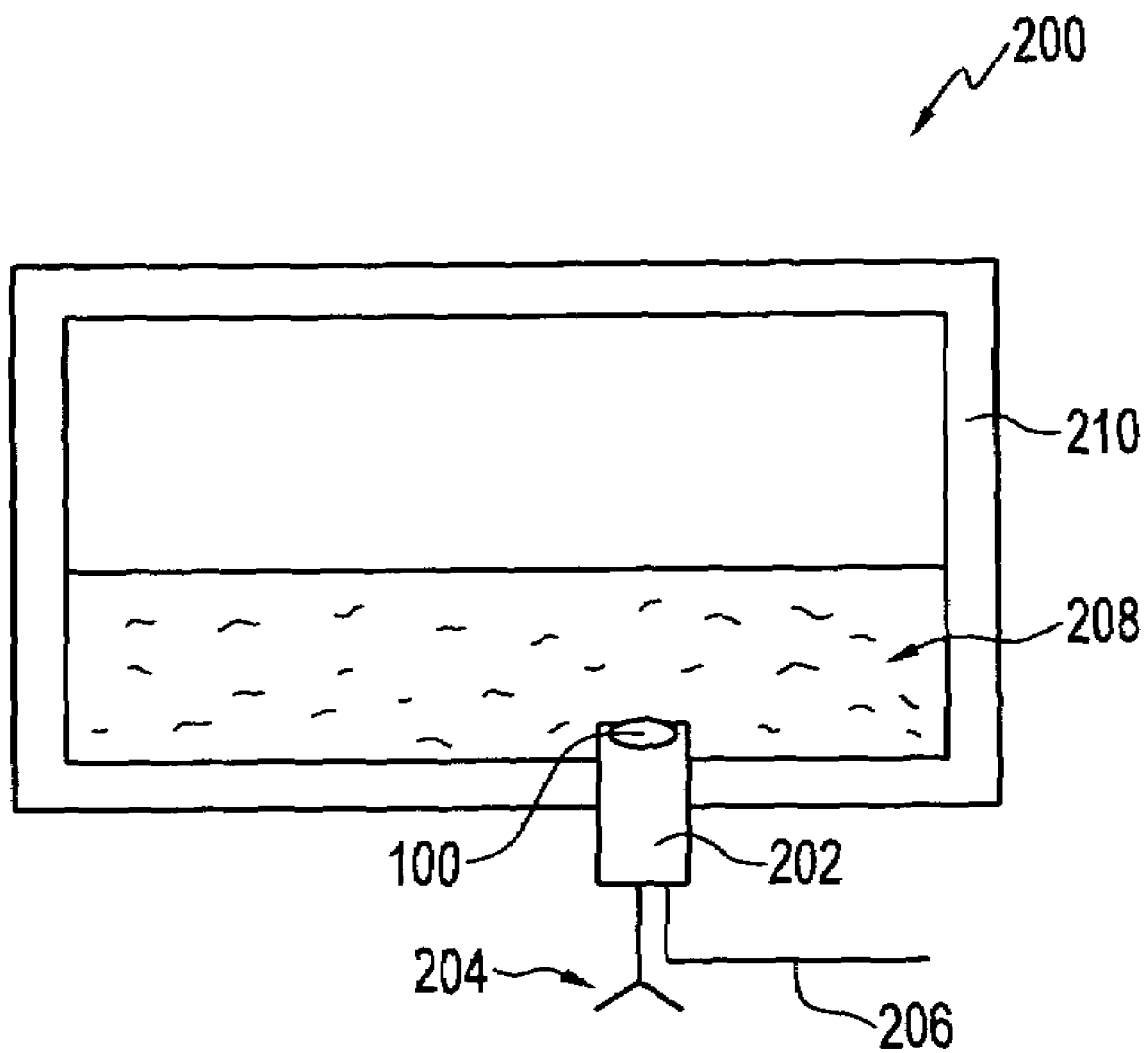
FIG. 2 illustrates a side view of a viscosity and corrosivity sensor system that can be implemented in accordance with a preferred embodiment.

FIG. 2 illustrates a side view of a viscosity and corrosivity sensor system 200 that can be implemented in accordance with a preferred embodiment. Note that in FIGS. 1–2, identical or similar parts or elements are generally indicated by identical reference numerals. System 200 incorporates the use of the viscosity and corrosivity sensor apparatus 100 depicted in FIG. 1. In system 200, the viscosity and corrosivity sensor apparatus 100 can be provided in the context of a bolt type sensor configuration 202 that is screwed directly into an engine 210. In this manner, the viscosity and corrosivity sensor apparatus 100 is exposed to a liquid 208 (e.g., oil) located in engine 210.

Note that engine 210 can be, for example, an automotive engine. Additionally, an antenna 204 can be connected to the bolt type sensor configuration 202 and hence the viscosity and corrosivity sensor apparatus 100. Antenna 204 thus provides the wireless transmission of data from and to the viscosity and corrosivity sensor apparatus 100. A wire 206 can be connected to other components not depicted in FIGS. 1–2, thereby providing for a wired application, in addition to the wireless communications capabilities offered by antenna 204. Wire 206 is optional, indicating that system 200 can be wired or wireless in nature.

The viscosity and corrosivity sensor apparatus 100 depicted in FIGS. 1–2 can be implemented in the context of an etch rate sensor. Electrodes 104 and/or 106 can be coated with a Cr—Ni—Fe alloy that mimics an alloy associated with engine 210, thereby function as an engine wear indicator. The viscosity and corrosivity sensor apparatus 100 reflects the amount that engine 210 is attached by acids associated with liquid or oil 208. Thus, cold or hot, powered or not, the viscosity and corrosivity sensor apparatus 100 is active at all times and provides accumulated data associated with engine wear information.

Note that substrate 102 can be provided as a piezoelectric substrate. Electrodes 104 and/or 106 can be provided as interdigital transducers patterned on substrate 102. Such interdigital transducers may launch and receive various acoustic waves, including a surface acoustic wave (SAW), also known in the art as a Rayleigh wave, and may also launch and receive several acoustic plate modes (APMs), depending upon design considerations.

Preferably, the selective material chosen to form the electrodes 104 and/or 106 has a reduced reactivity such that reaction products produced at the surface of the selective material are removed by the etchant. By utilizing a selective material having a reduced reactivity, the etched surface remains fresh during sensor operation, that is, the etched surface remains free from reaction products; unlike in conventional corrosivity sensors in which metal oxide or metal sulfides remain on the electrode surface reducing the active surface of the sensor apparatus 100. Since the sensing device 100 has a fresh surface for new reactions, the sensing device has a high sensitivity and a linear frequency response throughout the life time of the sensor apparatus 100.

Electrodes 104 and/or 106 can be implemented as etchable electrodes, depending upon design considerations. In one particular embodiment, for example, system 200 can be designed for use in automotive applications in which the etchant is degraded engine oil, which contains weak acids.

The etchable electrodes 104 and/or 106 for such an application can be fabricated by the deposition of iron (Fe) onto the substrate 103. Iron (Fe) has a reduced reactivity with the acids contained in the engine oil 208 such that reaction products, such as $Fe^{2+}$, are dissolvable in the oil.

Furthermore, oxides which may form on the deposited iron due to air exposure prior to the sensing device being placed in contact with the oil 208, such as for example $Fe_2O_3$ or FeO, react with the acids in the oil 208 in a similar manner as Fe. Other suitable reduced reactivity materials which may be utilized to fabricate the electrode 104 and/or 106 include iron (Fe), Nickel (Ni), manganese (Mn), cobalt (Co), chromium (Cr), vanadium (V), titanium (Ti), zinc (Zn), scandium (Sc), tin (Sn), magnesium (Mg) and Aluminum (Al). Or alternatively, metal alloys rich in one or more of these transition and non-transition metals.

Note that initially, the viscosity and corrosivity sensor apparatus 100 can be placed in its operating position in which electrode 104 and/or 106 is in contact with an etchant interest, in this case engine oil 208. An oscillating acoustic shear wave can be generated in the substrate 102 by applying an alternating voltage across electrodes 104 and 106. The resonant frequency can be initially measured. The etchant reacts with an etchable electrode 104 and/or 106 causing the mass loading of the viscosity and corrosivity sensor apparatus 100 to change and increasing the resonant frequency of the device over time. The resonant frequency of the apparatus 100 can be measured again after a given time period. The change in thickness of the selective material can be calculated theoretically or experimentally. The etch rate of the selective material can be determined by dividing the change in thickness by the given time period.

In an alternative embodiment of FIGS. 1–2, electrode 104 and/or 106 can be fabricated from an inactive material, such as, for example, Au, so that the oil 208 is unable to etch the electrodes 104 and/or 106. Alternatively, the inactive material can be copper (Cu), mercury (Hg), platinum (Pt), palladium (Pd), silver (Ag), iridium (Ir) or other similar inactive metals. Also, metal-nonmetal compounds (e.g., ceramic based on TIN, $CoSi_2$, or WC) can form the inactive electrode. Alternatively, the viscosity and corrosivity sensor apparatus 100 can be designed such that, in operation, the etchant is unable to contact another electrode 104 or 106, thereby rendering at least one of electrodes 104 or 106 inactive. For example, the electrode 104 can be coated with a protective layer, such as an insulating layer, to seal the electrode 104 from the etchant or the viscosity and corrosivity sensor apparatus 100 can be arranged such that only the selective material comes in contact with the etchant. Such scenarios, of course, represent alternative embodiments.

By preventing etching of one of the electrodes 104 or 106, reduction of the Q factor and increase in motional resistance of the device is limited. Since the substrate 102 (e.g., a quartz substrate) may also be possibly inactive to the acids contained in the oil 208, the viscosity and corrosivity sensor apparatus 100 can be highly sensitive to the effects of the oil etching the electrode 104 and/or 106. Utilizing an etchable electrode and/or etchable substrate instead of an inactive electrode and/or substrate is possible but may result in a less sensitive device.

The viscosity and corrosivity sensor apparatus 100 is useful for engine wear monitoring and oil quality detection because low temperature startability, fuel economy, and thinning or thickening effects at high/lower temperatures, along with lubricity and oil film thickness in running engines are factors dependent upon viscosity. Therefore, viscosity is a good indicator of an oil's ability to function properly. The viscosity and corrosivity sensing capabilities are thus provided in a single package. In a multi-function sensor design, the viscosity and corrosivity sensor apparatus 100 can be designed to detect both viscosity and corrosivity. Additionally, system 200 can include pressure, temperature, lubricity, conductivity, pH, humidity and/or particulate measurement capabilities depending upon design considerations.

The viscosity and corrosivity sensor apparatus 100 can be implemented in the context of a permanently installed oil sensor utilized for many different types of equipment such as, gasoline engines, diesel engines, natural gas engines, hydraulic systems, transmissions, compressors, turbines, and so forth. With monthly laboratory analysis, one only has 12 chances a year to catch a problem. Using a permanently installed oil sensor system (e.g., viscosity and corrosivity sensor apparatus 100) on a real time basis, one can increase his or her change of detecting an engine oil problem.

A permanently installed oil sensor system or viscosity and corrosivity sensor apparatus 100 can prove to be an effective configuration for monitoring and determining the condition of both lube and equipment. A sensor system or apparatus 100 may be utilized for monitoring the total amount of contamination present within lube oil by measuring the viscosity and TAN of the oil. Although complete laboratory analysis delivers a more detailed analysis of the oil, this sensor unit is highly efficient in determining whether the oil and equipment is in normal operating condition. When a problem with the equipment occurs, the unit may easily detect this problem by detecting the elevated TAN and viscosity of the oil due to the excess amount of contamination present within the lube oil. The permanently installed oil sensor system or apparatus 100 can be implemented as a simple monitoring tool that allows the automobile driver or maintenance personnel to know whether the equipment is within a "Normal" or "Abnormal" operating condition.

It is contemplated that the use of the present invention can involve components having different characteristics. It is intended that the scope of the present invention be defined by the claims appended hereto, giving full cognizance to equivalents in all respects.

What is claimed is:

1. A viscosity and corrosivity sensor apparatus, comprising:
   a substrate upon which at least one electrode is configured, wherein said at least one electrode is exposed to a liquid; and
   an oscillator connected to said at least one electrode, wherein said oscillator assists in providing data indicative of said corrosivity and data indicative of said viscosity of said liquid in contact with said at least one electrode, wherein said data indicative of said corrosivity is based on a frequency generated by said oscillator in association with said substrate and said at least one electrode, and said frequency is utilized to provide data indicative of an etch rate associated with said at least one electrode.

2. The apparatus of claim 1 further comprising a resistance measurement component connected to said at least one electrode and said oscillator, wherein said resistance measurement component obtains conductivity information associated with said liquid.

3. The apparatus of claim 1 wherein said data indicative of said viscosity of said liquid is based on an acoustic wave vibration amplitude or a damping resistance generated by said oscillator in association with said substrate and said at least one electrode.

4. The apparatus of claim 1 wherein said liquid comprises oil.

5. The apparatus of claim 1 wherein said at least one electrode is coated with at least one of the following: Cr, Ni, Fe, Mg, Al, Mn, Zn, Ti, Sn, V, Co, Sc, or Pb.

6. The apparatus of claim 1 further comprising an antenna connected to said apparatus, wherein said antenna wirelessly transmits and receives data for the detection of said viscosity and said corrosivity of said liquid.

7. A viscosity and corrosivity sensor system, comprising:
a substrate upon which at least one electrode is configured, wherein said at least one electrode is exposed to an oil and wherein said at least one electrode further comprises a top electrode and a bottom electrode configured upon said substrate;
an oscillator connected to said at least one electrode, wherein said oscillator assists in providing data indicative of said corrosivity and data indicative of said viscosity of said oil in contact with said at least one electrode, wherein said data indicative of said corrosivity is based on a frequency generated by said oscillator in association with said substrate and said at least one electrode, and said frequency is utilized to provide data indicative of an etch rate associated with said at least one electrode; and
an antenna connected to said system, wherein said antenna wirelessly transmits and receives data for the detection of said viscosity and said corrosivity of said oil.

8. The system of claim 7 wherein said oil comprises engine oil.

9. The system of claim 7 wherein said at least one electrode is coated at least one of the following: Cr, Ni, Fe, Mg, Al, Mn, Zn, Ti, Sn, V, Co, Sc, or Pb.

10. The system of claim 7 wherein said at least one electrode and said substrate comprise an acoustic wave sensor.

11. The system of claim 10 wherein said acoustic wave sensor comprises a quartz crystal microbalance (QCM) sensor device.

12. The system of claim 10 wherein said acoustic wave sensor comprises a Love wave sensor device.

13. The system of claim 10 wherein said acoustic wave sensor comprises a shear horizontal surface acoustic wave (SH-SAW) sensor device.

14. The system of claim 10 wherein said acoustic wave sensor comprises an acoustic plate mode (APM) sensor device.

15. The system of claim 10 wherein said acoustic wave sensor comprises a shear horizontal acoustic plate mode (SH-APM) sensor device.

16. The system of claim 7 wherein said acoustic wave sensor comprises a flexural plate mode acoustic wave sensor device.

17. A viscosity and corrosivity sensor method, comprising:
providing a substrate upon which at least one electrode is configured, wherein said at least one electrode is exposed to an oil and wherein said at least one electrode further comprises a top electrode and a bottom electrode configured upon said substrate;
electrically connecting an oscillator to said at least one electrode; and
electrically connecting a resistance measurement component to said at least one electrode and said oscillator, wherein said resistance measurement component generates conductivity information associated with said oil; and
providing an antenna in communication with said at least one electrode and said substrate, wherein said antenna wirelessly transmits and receives data indicative of said viscosity and said corrosivity of said oil, such that said oscillator assists in providing data indicative of said corrosivity and data indicative of said viscosity of said oil in contact with said at least one electrode, such that said data indicative of said corrosivity is based on a frequency generated by said oscillator in association with said substrate and said at least one electrode, and wherein said frequency also provides data indicative of an etch rate associated with said at least one electrode, and wherein said data indicative of said viscosity of said oil is based on an amplitude or a phase generated by said oscillator in association with said substrate and said at least one electrode.

18. The method of claim 17 wherein said at least one electrode is coated with at least one of the following: Cr, Ni, Fe, Mg, Al, Mn, Zn, Ti, Sn, V, Co, Sc, or Pb.

19. The method of claim 17 wherein said at least one electrode and said substrate comprise an acoustic wave sensor.

20. The method of claim 19 wherein said acoustic wave sensor comprises a flexural plate mode acoustic wave sensor device.

* * * * *